(12) United States Patent
Montoya, Jr.

(10) Patent No.: US 7,246,720 B1
(45) Date of Patent: Jul. 24, 2007

(54) CONDOM DISPENSING DEVICE

(76) Inventor: Gregory F. Montoya, Jr., 2623 Halelena Pl., Honolulu, HI (US) 96822

(*) Notice: Subject to any disclaimer, the term of this patent is extended or adjusted under 35 U.S.C. 154(b) by 282 days.

(21) Appl. No.: 11/076,771

(22) Filed: Mar. 10, 2005

(51) Int. Cl.
G07F 11/22 (2006.01)
B65H 3/00 (2006.01)

(52) U.S. Cl. .................. 221/275; 221/262; 221/229; 221/231

(58) Field of Classification Search ........... 221/226, 221/228, 229, 230, 231, 232, 259, 262, 275, 221/225
See application file for complete search history.

(56) References Cited

U.S. PATENT DOCUMENTS

| | | | | |
|---|---|---|---|---|
| 2,620,061 A * | 12/1952 | Uxa | ............ | 221/229 |
| 2,710,114 A | 6/1955 | Waber et al. | ............ | 221/232 |
| 2,853,206 A | 9/1958 | Uxa | | |
| 3,410,455 A | 11/1968 | Haas | ............ | 221/229 |
| 3,942,683 A | 3/1976 | Haas | ............ | 221/229 |
| 4,171,753 A | 10/1979 | Vreede | ............ | 221/197 |
| 4,295,579 A | 10/1981 | Haas | ............ | 221/229 |
| 4,986,442 A * | 1/1991 | Hinterreiter | ............ | 221/229 |
| 5,071,033 A | 12/1991 | Siwek | ............ | 221/229 |
| 5,080,258 A | 1/1992 | Hinterreiter | ............ | 221/198 |
| 5,310,084 A * | 5/1994 | Pittman | ............ | 221/150 A |
| 5,366,112 A | 11/1994 | Hinterreiter | ............ | 221/198 |
| 5,447,253 A | 9/1995 | Williams | ............ | 221/927 |
| 5,713,488 A | 2/1998 | Farrugia | ............ | 221/45 |
| 6,230,931 B1 * | 5/2001 | Mandle et al. | ............ | 221/247 |
| 6,564,967 B1 * | 5/2003 | Stringfield et al. | ............ | 221/229 |

FOREIGN PATENT DOCUMENTS

| | | |
|---|---|---|
| CA | 2130536 | 2/1996 |
| IT | WO93/21611 | 10/1993 |

* cited by examiner

Primary Examiner—Gene O. Crawford
Assistant Examiner—Timothy Waggoner
(74) Attorney, Agent, or Firm—Sturm & Fix LLP

(57) ABSTRACT

A condom dispensing device (10) including an outer hollow sleeve member (20) that slidably receives a feed unit (12) that includes a three sided feeder body member (30) having a spring biased elevator element (34) supporting a stack of condoms that are delivered to a dispensing unit (13) including a cap member (43) provided with a rack gear (44) that is pivotally connected to the feeder body member (30) and engageable with a pusher plate member (40) that delivers condoms through a feeder aperture (35) wherein, the cap member (43) and the outer hollow sleeve member (20) have a complementary appearance that disguises the purpose and the function of the condom dispensing device (10).

16 Claims, 2 Drawing Sheets

CONDOM DISPENSING DEVICE

BACKGROUND OF THE INVENTION

1. Field of the Invention

The present invention relates to the field of condom dispensing device in general and in particular to a personal condom dispenser device, the utilitarian purpose of which is not readily apparent upon visual inspection.

2. Description of Related Art

As can be seen by reference to the following U.S. Pat. Nos. 2,620,061; 2,853,206; 4,966,305; 4,171,753; and, 4,295,579, the prior art is replete with myriad and diverse condom dispensing devices.

While all of the aforementioned prior art constructions are more than adequate for the basic purpose and function for which they have been specifically designed, they are uniformly deficient with respect to their failure to provide a simple, efficient, and practical condom dispenser the utilitarian purpose of which is not readily discernible from mere visual inspection of its external appearance.

As most sexually active individuals are all too well aware, the blatant display of condoms on a night stand or the like creates a somewhat awkward atmosphere for that individual's sexual partner and has a tendency to at least initially inhibit their incipient amorous adventure.

As a consequence of the foregoing situation, there has existed a longstanding need among sexually active adults for a new and improved device for storing and dispensing condoms in a discreet fashion from a dispensing device the purpose of which is disguised until the optimum moment arrives; and, the provision of such a device is the stated objective of the present invention.

BRIEF SUMMARY OF THE INVENTION

Briefly stated, the condom dispensing device that forms the basis of the present invention comprises in general a housing unit, a dispensing unit and a feed unit which delivers a stack of condoms to the dispensing unit which will eject the uppermost condom in a sequential fashion from the housing unit.

As will be explained in greater detail further on in the specification, the dispensing unit is pivotally connected to the feed unit which is slidably received within the housing unit wherein, both the dispensing unit and the housing unit have a decorative appearance that disguises the true purpose and function of the condom dispensing device.

This allows the condom dispensing device to be openly displayed in an unobtrusive fashion without any negative inferences being drawn by either a casual visitor or prospective sexual partner observing the presence of this ertswhile object d' art in a person's bedroom, while also insuring that a condom will be handy at the appropriate time.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
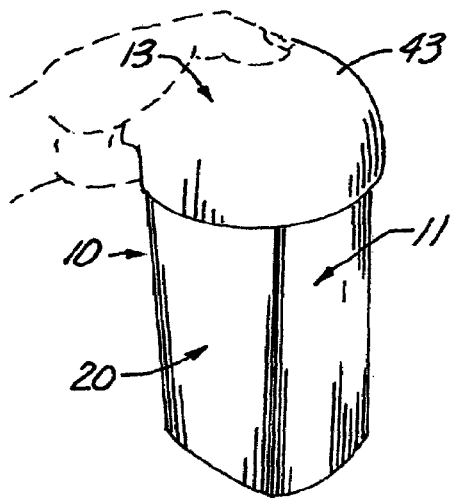
FIG. 1 is a perspective view of the condom dispensing device immediately prior to actuation.
Figure 2:
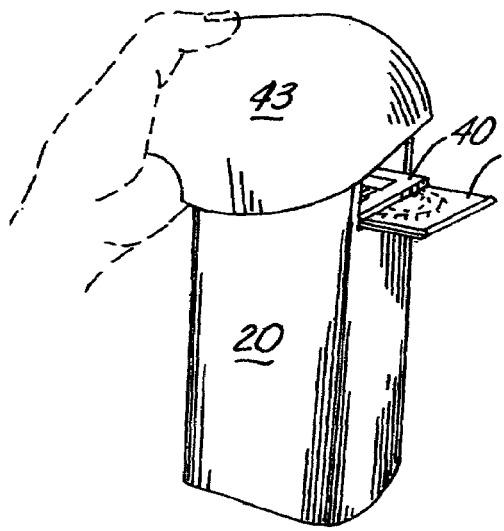
FIG. 2 is a perspective view of the condom dispensing device at the end of the dispensing sequence.
Figure 4:
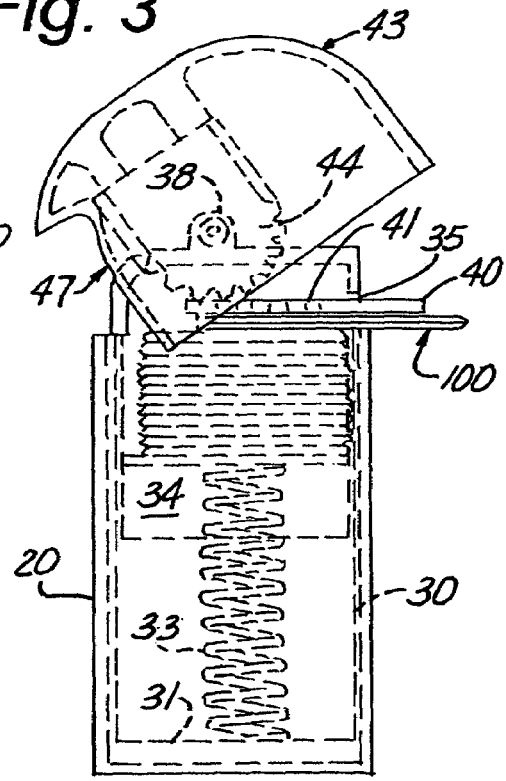
FIG. 4 is a side elevation view showing the structural components in phantom at the end of the dispensing sequence; and, FIG. 5 is a cross-sectional perspective view showing the internal structural components depicted in phantom in FIG. 4.

As can be seen by reference to the drawings, and in particular to FIGS. 1 and 4, the condom dispensing device that forms the basis of the present invention is designated generally by the reference number 10. The dispensing device 10 comprises in general a housing unit 11, a feed unit 12, and a dispensing unit 13. These units will now be described in seriatim fashion.

As can be seen by reference to FIGS. 1 and 3, the housing unit 11 comprises an outer hollow sleeve member 20 that is dimensioned to slidably receive a substantial portion of the feed unit 12 which will now be described in detail.

Figure 3:
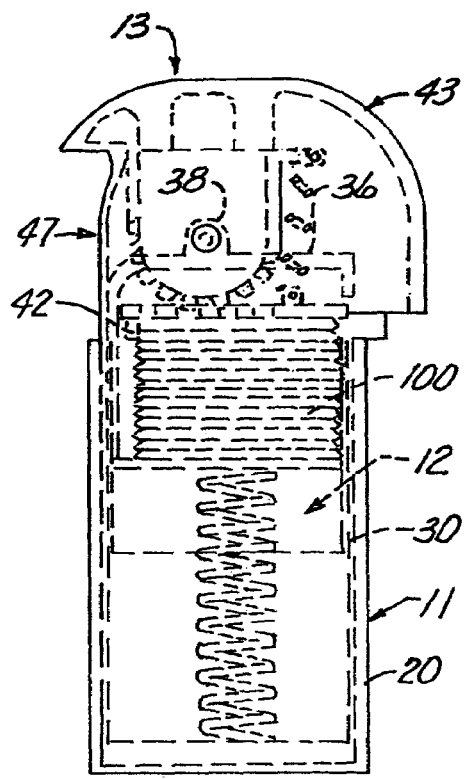
FIG. 3 is a side elevation view showing the structural components in phantom prior to actuation.
Figure 5:
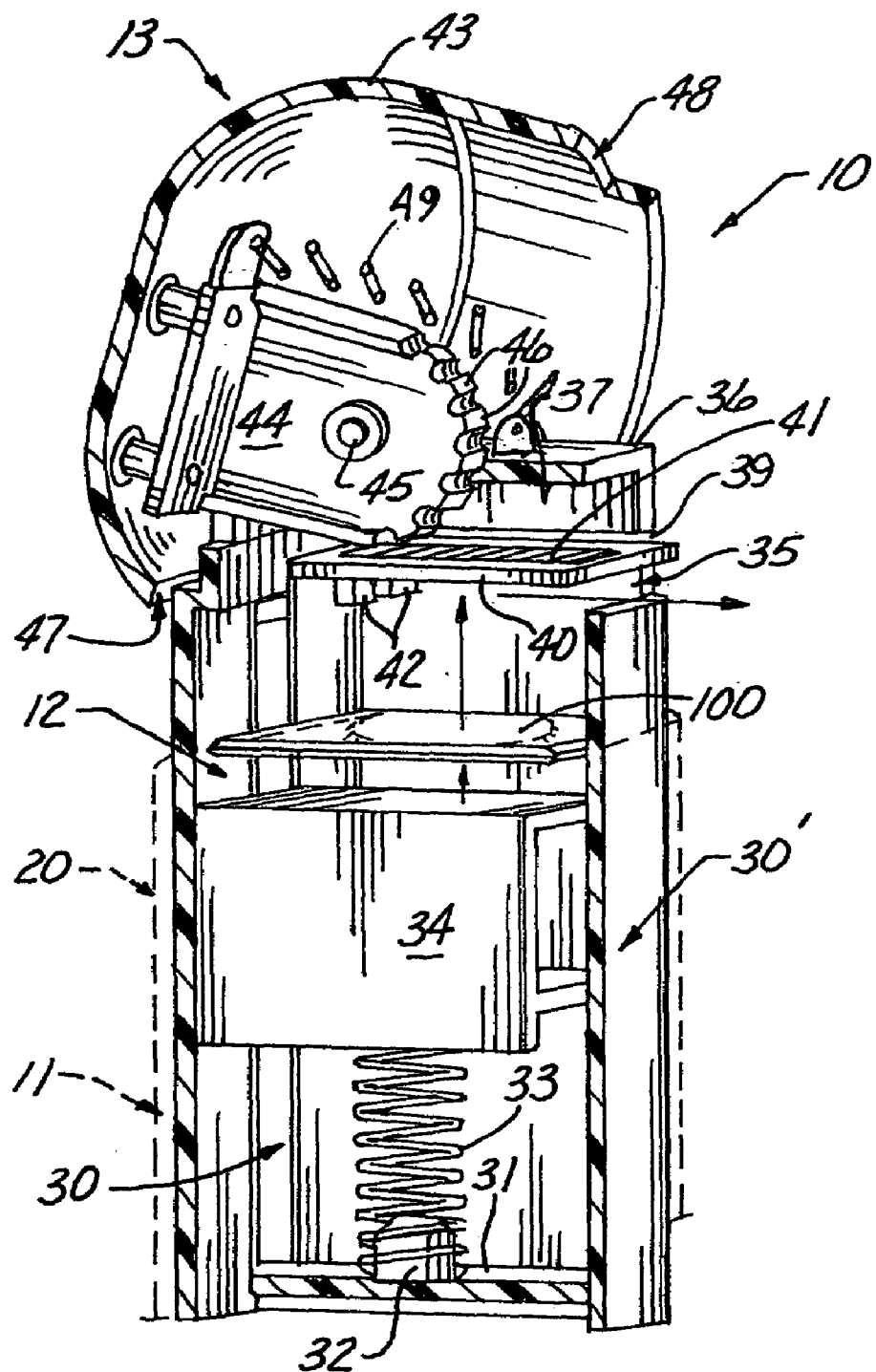

Turning now to FIGS. 3 through 5, it can be seen that the feed unit 12 comprises a three sided feeder body member 30 having a base 31 provided with a generally cylindrical post 32 that supports a spring biasing element 33 the upper surface of which bears against the bottom of an elevator element 34 that is slidably disposed within the feeder body member 30 wherein, the top surface of the elevator element is dimensioned to receive a stack of individual sealed condoms 100.

In addition, the front of the feeder body member 30 is provided with an enlarged aperture 35 dimensioned to allow a condom 100 to pass under the influence of the dispensing unit 13 as will be explained further on in the specification.

Still referring to FIGS. 3 through 5, it can be seen that the upper portion of the feeder body member 30 is generally enclosed on four sides by outer body sleeve member 20 wherein, the top surface 36 of the feeder body member 30 is provided with an elongated aperture 37 that is flanked by a pair of apertured hubs 38 the purpose and function of which will be described presently.

Furthermore, as can best be seen by reference to FIG. 5, the upper portion of the feeder body member 30 is also provided with a pair of opposed horizontal recesses 39 that intersect the front aperture 35 of the feeder body member 30 wherein, the purpose and function of these opposed recesses will be explained next.

As can also be appreciated by reference to FIGS. 3 through 5, the dispensing unit 13 comprises a pusher plate member 40 slidably disposed in the opposed horizontal recesses 39 in the feeder body member 30 wherein, the upper surface of the pusher plate member 40 is provided with a series of grooves 41 and the bottom trailing edge of the pusher plate member 40 is provided with a downwardly depending lip 42 adapted to engage the inboard end of a sealed condom 100.

In addition, the dispensing unit 13 includes a decorative cap member 43 operatively associated with the pusher plate member 40 via a centrally disposed and downwardly depending rack gear 44 pivotally secured to the hubs 38 of the hollow feeder body member 30 via an axle element 45 wherein, the teeth 46 of the rack gear 44 are engageable with the series of grooves 41 on the pusher plate member 40. Furthermore, a spring biasing element 49 is operatively connected between the rack gear 44 and the top surface 36 of the feeder body member 30 to spring bias the decorative cap member 43 into a normally closed position. This action of the rack gear 44 reciprocates the pusher plate member 40 back and forth in the opposed horizontal recesses 39 in the upper portion of the feeder body member 30 in a well recognized manner to sequentially feed the uppermost condom 100 from the stack of condoms supported on the elevator element 34 in an equally well recognized fashion.

It should further be noted by reference to FIGS. 3 through 5, that the decorative cap member 43 has a trailing edge provided with a recessed aperture 47 to permit the backward pivoting of the cap member 43 relative to both the hollow sleeve member 20 and the feeder body member 30, and the front face of the cap member 43 may also be provided with a discrete recess 48 that is alignable with the front aperture 35 of the feeder body member 30.

As was mentioned previously, both the cap member 43 and the sleeve member 20 have a complementary exterior appearance that effectively disguises the purpose and function of the condom dispensing device 10.

In use, all that is necessary is for a person to pivot the cap member 43 rearwardly causing the rack gear 44 to engage the pusher plate member 40 in a forward direction such that the lip 42 of the pusher plate member 40 will force a single sealed condom 100 to be delivered through the feed aperture 35 of the feeding unit 12.

Then when it is necessary to replenish the supply of condoms 100, the cap member 43 is grasped and lifted upwardly to raise the feeder body member 30 out of the hollow sleeve member 20 such that a new supply of sealed condoms 100 can be deposited on the top of the elevator element 34 through the open side designated generally as 30' of the three sided feeder body member 30.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A condom dispensing device for the unobtrusive and discreet storage and dispensing of condoms wherein, the dispensing device comprises a housing unit including a hollow sleeve member having a first aesthetically pleasing appearance;
    a feed unit including a feeder body member dimensioned to be slidably received in said hollow sleeve member and containing a spring biased elevator element adapted to support a stacked plurality of sealed condoms;
    a dispensing unit including a cap member having a second aesthetically pleasing appearance that is complementary to said first aesthetically pleasing appearance of the hollow sleeve member;
    means associated with said feed unit for sequentially ejecting condoms from said feeder body member;
    wherein, said means comprises in part a pusher plate member having a trailing edge provided with a downwardly depending lip; and
    wherein, said feeder body member has a pair of opposed horizontal recesses and said pusher plate member is slidably disposed in said pair of recesses.

2. The device as in claim 1; wherein, said means comprises in part a pusher plate member having a trailing edge provided with a downwardly depending lip.

3. A condom dispensing device for the unobtrusive and discreet storage and dispensing of condoms wherein, the dispensing device comprises a housing unit including a hollow sleeve member having a first aesthetically pleasing appearance;
    a feed unit including a feeder body member dimensioned to be slidably received in a hollow sleeve member and containing a spring biased elevator element adapted to support a stacked plurality of sealed condoms;
    a dispensing unit including a cap member having a second aesthetically pleasing appearance that is complementary to said first aesthetically pleasing appearance of the hollow sleeve member;
    means associated with said feed unit for sequentially ejecting condoms from said feeder body members;
    wherein, said cap member is operatively associated with said means for sequentially ejecting condoms from said feeder body member;
    wherein, said means comprises in part a pusher plate member having a trailing edge provided with a downwardly depending lip; and
    wherein, said feeder body member has a pair of opposed horizontal recesses and said pusher plate member is slidably disposed in said pair of recesses.

4. The device as in claim 3; wherein, said pusher plate member has a top surface provided with a plurality of grooves and said cap member has a rack gear adapted to engage said plurality of grooves.

5. The device as in claim 4; wherein, said feeder body member has an upper portion and the rack gear on the cap member is pivotally associated with the upper portion of the feeder body member.

6. The device as in claim 5; wherein, the upper portion of the feeder body member is provided with an elongated aperture flanked by a pair of apertured hubs.

7. The device as in claim 6; wherein, the rack gear is dimensioned to be received within said elongated aperture.

8. The device as in claim 7; wherein, the rack gear is pivotally connected to said apertured hubs via an axle element.

9. The device as in claim 1; wherein, the feeder body member has a generally three sided configuration that defines a generally open fourth side.

10. The device as in claim 9; wherein, said generally open fourth side is dimensioned to receive a plurality of condoms.

11. The device as in claim 8; wherein, said generally open fourth side is dimensioned to receive a plurality of condoms.

12. The device as in claim 11; wherein, said generally open fourth side is dimensioned to receive a plurality of condoms.

13. The device as in claim 10; wherein, said feeder body member has a front face provided with a feeding aperture.

14. The device as in claim 13; wherein, said feeding aperture is perpendicularly aligned with said pair of opposed recesses.

15. The device as in claim 12; wherein, said feeder body member has a front face provided with a feeding aperture.

16. The device as in claim 15; wherein, said feeding aperture is perpendicularly aligned with said pair of opposed recesses.

* * * * *